United States Patent
Nohda

[11] 3,969,019
[45] July 13, 1976

[54] CURVATURE MEASURING OPTICAL SYSTEM IN OPHTHALMOMETER

[75] Inventor: Masao Nohda, Kawasaki, Japan
[73] Assignee: Nippon Kogaku K.K., Tokyo, Japan
[22] Filed: Apr. 7, 1975
[21] Appl. No.: 565,619

[52] U.S. Cl. ................................. 351/13; 351/14; 356/156
[51] Int. Cl.² .......................................... A61B 3/02
[58] Field of Search ....................... 351/13, 14, 39; 356/156, 127

[56] References Cited
UNITED STATES PATENTS

| | | | |
|---|---|---|---|
| 864,769 | 9/1907 | Brewer | 351/13 X |
| 890,580 | 6/1908 | Sutcliffe | 351/13 |
| 1,523,528 | 1/1925 | Henker | 351/13 X |
| 1,918,540 | 7/1933 | Hautinger | 351/13 |

*Primary Examiner*—Paul A. Sacher
*Attorney, Agent, or Firm*—Shapiro & Shapiro

[57] ABSTRACT

A curvature measuring optical system in an ophthalmometer comprises a first and a second lens group and rotary prisms disposed between the two lens groups. The first lens group has the focal point thereof lying at the location of the virtual image of an index projected on the cornea of an eye to be examined. The second lens group focuses on the focal plane thereof a light beam made parallel by the first lens group. The rotary prisms separate the image into two images and are rotatable in the opposite directions from each other. The optical system is improved in that it further includes a light-intercepting member formed with at least three openings and disposed just behind the first lens group to divide the light beam between the two lens groups, and that the rotary prisms are a first rotary prism member disposed adjacent the second lens group and just behind one of the openings to cause a light beam passed through the one opening to be deflected on the focal plane in a predetermined direction and a second rotary prism member disposed adjacent the second lens group and just behind another one of the openings to cause a light beam passed through said another opening to be deflected on the focal plane in a direction perpendicular to direction of deflection by the first rotary prism member. The two rotary prism members may be rotated by rotating means therefor.

3 Claims, 6 Drawing Figures

CURVATURE MEASURING OPTICAL SYSTEM IN OPHTHALMOMETER

BACKGROUND OF THE INVENTION

1. Field of the Invention

This invention relates to an ophthalmometer which can measure the curvature radius of the cornea of a subject's eye with high accuracy by simple operation.

2. Description of the Prior Art

The ophthalmometer is a device for measuring the size of an index image projected upon the cornea of an eye to thereby measure the curvature radius of the cornea. Generally, the cornea is an elliptical surface and has two curvature radii, namely, a maximum curvature radius and a minimum curvature radius orthogonal thereto. Measurement of these two curvature radii will hereinafter be referred to as "cornea astigmatism measurement." There have heretofore been many types of the cornea astigmatism measurement, each of which has its own merits and demerits. The most typical conventional methods of cornea astigmatism measurement will hereinafter be described by reference to FIGS. 1 and 2 of the accompanying drawings.

FIG. 1 shows what is called Sutcliffe type ophthalmometer, in which the image of an index 2 is formed on the cornea of a subject 1 by an illuminating system, not shown, and the image of the index reflected by the cornea enters a lens 3. An aperture plate 4 having four openings formed therein is disposed just behind the lens 3 so that a light beam is divided into four beams. Across two of these light beams, two declination prisms 5a and 5b are respectively disposed for movement in the direction of the optical axis and moreover, these prisms are oriented in such a manner that their bases are 90° out of phase with each other and the base surfaces are parallel to the optical axis. When the image of the index 2 reflected by the cornea is focused on a focusing plate 6, three images of the index 2 may be seen through an eyepiece 7 because two of the four openings are aligned with each other. These three index images may be aligned with one another by moving the prisms 5a and 5b, and the amounts of movement of these prisms may be read as curvature radii, whereby cornea astigmatism may be measured.

Thus, the ophthalmometer of this type has an advantage that it can measure the curvature radii on the two axes of the cornea, but since the prisms 5a and 5b are moved between the aperture plate 4 and the focusing plate 6, the center thickness, deflection angles and directions of movement of these prisms 5a and 5b all affect the measurement, This makes the device not only difficult to manufacture but also poor in accuracy.

FIG. 2 shows another known device which is called Hartinger type ophthalmometer. A feature of the ophthalmometer of this type is that two sets of rotary prisms 5a and 5b each comprising a prism having a center portion performing a deviation opposite to that of the peripheral portion are disposed across a parallel light beam to separate into two images the index image reflected by the cornea. To form the parallel light beam, a first lens 3a is disposed in such a manner that the focal point thereof lies at the location whereat the virtual image of the index projected upon the cornea is focused. The images separated by the rotary prisms are passed through a second lens 3b and thereby focused on a focal plane 6. Thereupon, the rotary prisms 5a and 5b are rotated in the opposite directions by rotating means, so that the two separate images are aligned with each other in a predetermined relationship. A certain relationship is maintained between the angles of rotation and the curvature radius of the cornea and the angles of rotation are read, whereby the curvature radius may be known. According to such design, the above-noted disadvantages may be overcome since the prisms are merely rotated, whereas in the cornea astigmatism measurement of the subject's eye 1, it is only the curvature radius on one of the two axes that can be measured and therefore, measurement of the curvature radius on the other axis presupposes taking the trouble to rotate the entire optical system by 90°, which in turn means much procedure involved in the measurement.

SUMMARY OF THE INVENTION

The present invention has, for its object, to provide a curvature measuring optical system for ophthalmometer which can measure the curvature radii on two axes at a time and which is easy to manufacture and high in measurement accuracy.

The invention will become more fully apparent from the following detailed description thereof taken in conjunction with the accompanying drawings.

DESCRIPTION OF THE PREFERRED EMBODIMENTS

Figure 1:
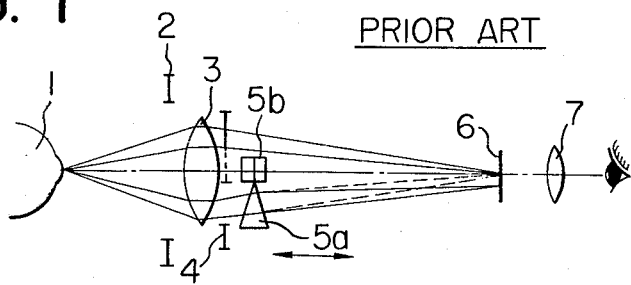
FIGS. 1 and 2 schematically show the optical systems of ophthalmometers according to the prior art.
Figure 2:
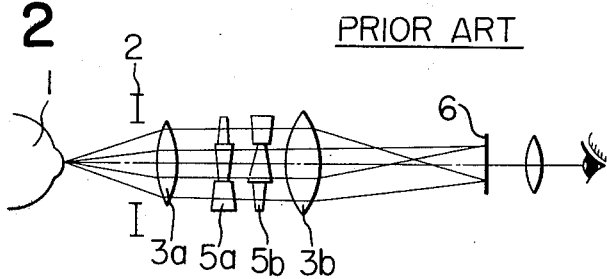
Figure 4:
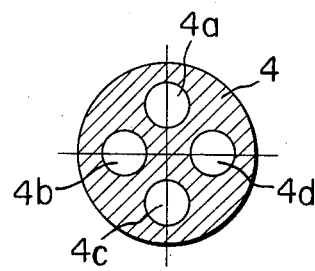
FIG. 4 shows a form of the index.
Figure 5:
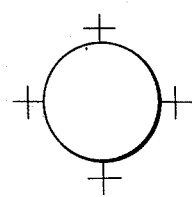
FIG. 5 is a front sectional view of the aperture plate in the embodiment of FIG. 3.
Figure 3:
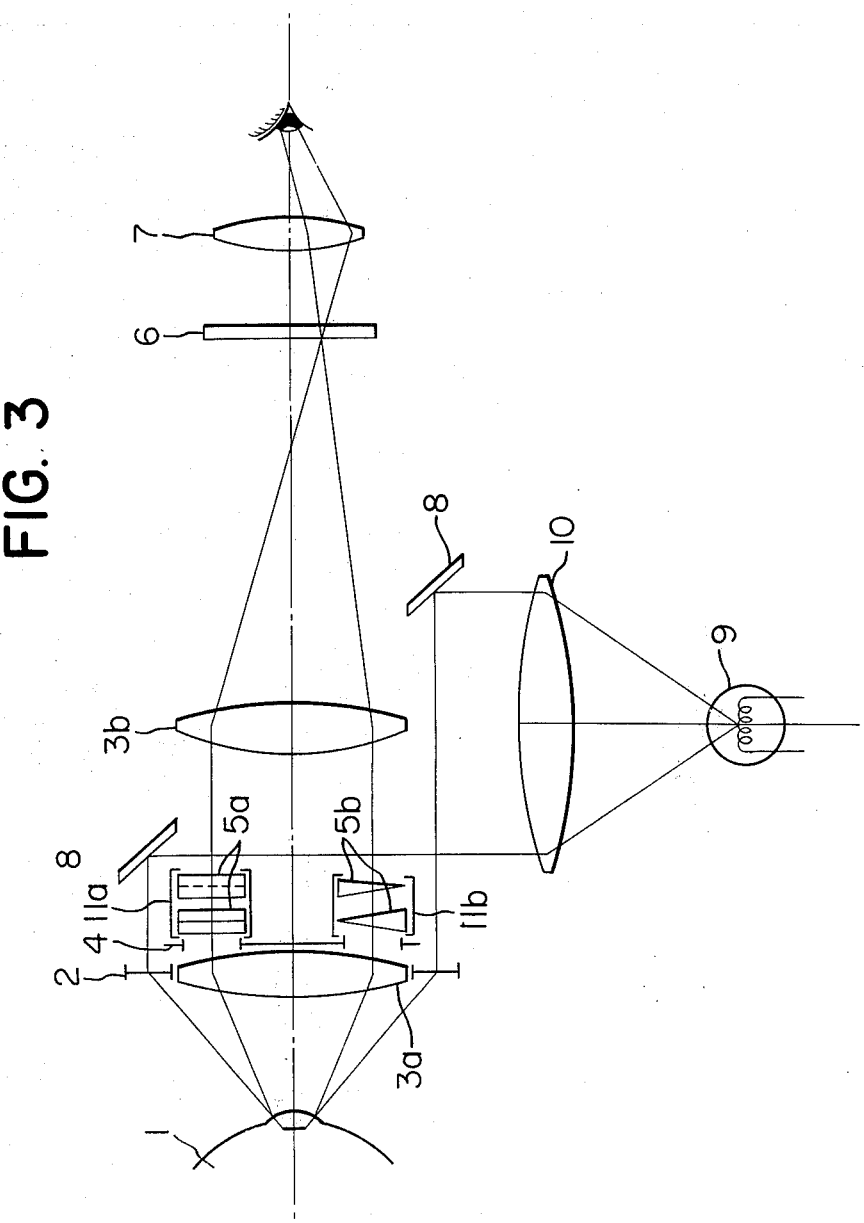
FIG. 3 schematically shows an optical system according to an embodiment of the present invention.

In FIG. 3, numeral 1 designates a subject's eye, and the image of an index 2 as shown in FIG. 4 is formed on the cornea of the subject's eye 1 by a light source 9, an illuminating lens 10 and a mirror 8 which is not mirror-surfaced in the middle thereof. The virtual image of the index reflected by the cornea is made into a parallel light beam by a lens 3a. Designated by numeral 4 is a aperture plate formed with four apertures 4a – 4d and disposed adjacent that side of the lens 3a which is remote from the cornea. Designated by 5a and 5b are rotary prisms each comprising two prisms movable against each other. The rotary prisms 5a and 5b are respectively rotated by rotating means 11a and 11b which are rotatable in the light beam and in a direction perpendicularly transverse to the light beam. The rotary prism 5a is disposed just behind the opening 4c of the aperture plate. Further, the rotary prisms 5a and 5b are oriented with their bases being 90° out of phase with each other. Thus, the light beam passed through the prisms 5a and 5b will be deflected in a vertical direction and in a direction perpendicular to the plane of the drawing sheet. Designated by 3b is a lens for focusing on the focal plane 6 the light beam passed through the rotary prisms 5a, 5b and the openings 4b, 4d. Numeral 7 designates an eyepiece for enlarging the image of the index reflected by the cornea and focused on the focal plane 6.

Figure 6:
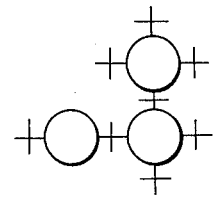
FIG. 6 shows the field of view.

In operation, the reflected light of the index 2 reflected by the cornea is made into a parallel light beam by the lens 3a, and the parallel beam is divided into four beams by the aperture plate 4. Of these four beams, the two beams which do not pass through the prisms 5a and 5b are passed through the lens 3b and focused on the focal plane 6 in alignment with each other. The other two beams passed through the rotary prisms 5a and 5b are not focused on the center of the focal plane 6 under the influence of these prisms. More specifically, assuming that the light beam passed through the rotary prism 5b is focused vertically of the focal plane in the plane of the drawing sheet, the light beam passed through the prism 5a is focused on the focal plane in a direction perpendicular to the drawing sheet. If these images are viewed through the eyepiece 7, they will appear in the manner as shown in FIG. 6 by aligning the image formed through the prism 5a with the light beam focused not through the prism in a predetermined relationship. Since the degree to which the light beam passed through the prism 5a is deflected is proportional to the angle of rotation of the rotary prism 5b, the curvature radius of the cornea in the vertical direction can be known from the angle of rotation of the rotary prism 5b.

Likewise, the curvature radius of the cornea in the horizontal direction can also be known from the angle of rotation of the rotary prism 5a. Thus, the cornea astigmatism measurement has been accomplished.

According to the present invention, as described above, there may be provided an opthalmometer which can measure the curvature radii on two axes at a time and with high accuracy through a simple construction.

I claim:

1. In a curvature measuring optical system in an ophthalmometer comprising a first lens group having a focal point thereof lying at the location of the virtual image of an index projected on the cornea of an eye to be examined, a second lens group for focusing on the focal plane thereof a light beam made parallel by said first lens groups, and rotary prisms disposed between said first and said second lens group to separate the image into two images and rotatable in the opposite directions from each other, whereby said rotary prisms may be rotated by a rotating member therefor to align the separate reflected images with each other on the focal plane in a predetermined relationship, thereby measuring the curvature radii of the cornea from the angles of rotation of said rotary prisms, the improvements residing in the provision of a light-intercepting member formed with at least three openings and disposed just behind said first lens group to divide the light beam between said first and said second lens group, a first rotary prism member disposed just behind one of the openings in the light-intercepting member to receive the light passing through the first lens group and said one opening and to cause a light beam corresponding to said one opening to be deflected on the focal plane in a predetermined direction, a second rotary prism member disposed just behind another one of said openings to receive the light passing through the first lens group and said another opening and to cause a light beam corresponding to said another opening to be deflected on the focal plane in a direction perpendicular to the direction of deflection by said first rotary prism member, and means for measuring the respective angle of rotation of said first and second rotary prism members.

2. A curvature measuring optical system according to claim 1, wherein said first and said second rotary prism member are oriented with the bases thereof being 90° out of phase with each other.

3. A curvature measuring optical system according to claim 1, wherein four of said openings are formed in said light-intercepting member, and one of said four openings which has none of said rotary prism members is indicated as the image of an index when the virtual image of the index projected on said cornea is focused on the focal plane.

* * * * *